United States Patent [19]

McFarlane

[11] Patent Number: 4,956,143

[45] Date of Patent: * Sep. 11, 1990

[54] METHOD AND APPARATUS FOR THE MULTI-UNIT PRODUCTION OF THIN-WALLED TUBULAR PRODUCTS UTILIZING AN INJECTION MOLDING TECHNIQUE

[75] Inventor: Richard H. McFarlane, Geneva, Ill.

[73] Assignee: Taut, Inc., Geneva, Ill.

[ * ] Notice: The portion of the term of this patent subsequent to Jun. 14, 2005 has been disclaimed.

[21] Appl. No.: 271,886

[22] Filed: Nov. 16, 1988

Related U.S. Application Data

[60] Continuation-in-part of Ser. No. 25,646, Mar. 13, 1987, which is a continuation-in-part of Ser. No. 496,979, May 23, 1983, abandoned, which is a division of Ser. No. 302,490, Sep. 16, 1981, abandoned.

[51] Int. Cl.⁵ .............................................. B29C 33/30
[52] U.S. Cl. .................................... 264/334; 425/150; 425/468; 425/575; 425/577; 425/588
[58] Field of Search ............... 249/122, 124, 125, 142; 425/142, 144, 146–151, 573, 577, 581, 574–576, 588, 468; 264/334, 297.2, 328.1, 328.8, 328.11, 40.5

[56] References Cited

U.S. PATENT DOCUMENTS

| | | | |
|---|---|---|---|
| 4,268,243 | 5/1981 | Koshkin et al. | 425/575 |
| 4,332,545 | 6/1982 | Cargile | 425/577 |
| 4,750,877 | 6/1988 | McFarlane | 425/573 |

Primary Examiner—Jill L. Heitbrink
Attorney, Agent, or Firm—Malloy, Downey & Malloy

[57] ABSTRACT

Thin-walled elongated tubular products are individually formed utilizing injection molding of a plastic melt into a mold cavity having an elongated core pin maintained in substantially centered relation on the interior thereof through the application of tension continuously being applied coaxially to the core pin. Multi-unit or mass production techniques include use of a plurality of mold cavities each successively subjected to receiving a hot plastic melt injection wherein the resulting formed product is, through successive steps, removed from the mold cavity, trimmed, separated from the core pin, and possibly further processed for depositing in collection facilities or transferred to other processing steps. Concurrently, each mold cavity and associated core pin are initially separated, processed separately and reunited for continued and repeated use and further subjected to precise and preprogrammed positioning relative to the inflow of plastic melt in order to overcome any imbalance or inconsistency in flow characteristics of the flow of the hot melt into the mold cavity.

12 Claims, 6 Drawing Sheets

METHOD AND APPARATUS FOR THE MULTI-UNIT PRODUCTION OF THIN-WALLED TUBULAR PRODUCTS UTILIZING AN INJECTION MOLDING TECHNIQUE

BACKGROUND OF THE INVENTION

This is a continuation-in-part application of copending patent application Ser. No. 025,646, filed Mar. 13, 1987 which is a continuation-in-part application of copending patent application Ser. No. 496,979, filed May 23, 1983, now abandoned, which is a divisional application of then copending application Ser. No. 302,490, filed Sept. 16, 1981, now abandoned.

FIELD OF THE INVENTION

An apparatus and method for the multi-unit or mass production of thin-walled plastic tubular products such as medical catheters necessitating precise and consistent dimensional and configurational characteristics wherein an extremely small diameter bore is maintained along a thin walled product throughout a majority of the length of the product. An apparatus and method for successively utilizing an injection molding technique with a plurality of associated core pins and mold cavities which are first separated and independently processed during the processing steps performed on the product itself and subsequently reunited and subjected to selective preprogrammed positioning relative to the aforementioned injection molding facility in order to overcome any imbalance in flow characteristics between the associated core pin and mold cavity.

DESCRIPTION OF THE PRIOR ART

There is a need in the art of molding plastic products to be able to produce a product having a relatively small diameter hole extending therethrough and along a significant length thereof. An example of such a product is a medical catheter comprising a jacket or sleeve of plastic material through which a needle is to be inserted during its use. Especially in the field of medical products, it is important to exert great care in maintaining high quality and dimensional requirements in the finished product. Particularly, in catheter type devices, an elongated tubular product requires that a substantially centrally located straight line hole be formed wherein the wall thickness of the catheter product should be carefully controlled and regulated during the formation process to accomplish a consistent flex pattern. More specifically, maintenance of a central bore throughout the formed product having a straight line configuration has the effect of causing the shank portion of the tubular product to be maintained in a preferred and even required straight line configuration. Variance from this straight line configuration along the length of the tubular product will result in a defective, unusable product. There are of course numerous other situations in which a relatively fine, small diameter hole is required to be formed through a tubular plastic molded part whether the hole is substantially centered within the part or not, or whether the part is cylindrical or not. Generally the term "tubular" as used herein refers to parts which have at least one fine hole therethrough. Often times, such molded plastic parts are required to have a thin wall of necessarily controlled thickness with a straight line longitudinal channel, having an exceptionally small diameter, extending therethrough.

Previously, especially in the art of injection molding, when plastic is melted, and forced to flow into a cavity about a fine, small diameter core, the pressure of injection or forcing the melt into the mold cavity during the molding operation tends to cause the thin diameter core to be displaced from its straight line configuration relative to the central axis of the mold cavity. Such displacement may also occur when there is an imbalance in the flow of melt along at least a portion of the mold cavity and core pin. This displacement renders the tubular product defective since any significant displacement of the core pin from its straight line configuration causes the tubular shank of the finished product to be offset from a required straight line configuration. Accordingly, the prior art has generally been limited to relatively short tubular lengths in relation to the diameter of the hole through it. If, for example, the tubular product is to be relatively long, which is quite common in the medical industry, a small hole, especially a hole in a thin walled tube is extremely difficult to make with any great degree of accuracy. In addition, different materials provide different problems.

Accordingly, in the formation of the type products referred to above, a primary difficulty has been that the core pin must be of an extremely small diameter and therefore subject to pressures of the inflowing melt forced into the mold cavity utilizing injection molding techniques. The pressure or force of the incoming melt exerts a force on the fine, very thin core pin frequently resulting in a displacement from its straight line configuration and substantially centered orientation with the mold cavity and the production of a defective thin walled tubular product.

Another problem generally associated with the injection molding technique of products of the type referred to herein is the breakdown in the integrity of the plastic material utilized to form the tubular product when the material is raised to a relatively high temperature and/or forced to travel along what may be referred to as a circuitous path from the point of leaving the injection nozzle to the point of entering and passing along the length of the mold cavity. This is particularly true when the plastic material, after being melted, is forced to travel along a circuitous path or path including one or more right angles at a relatively high speed. However, when using injection molding techniques at relatively slow speeds, the material must be raised to a somewhat higher than normal temperature prior to injection. This higher temperature frequently results in a degrading of the material.

All of the above factors and limitations are present in and in fact become of much greater concern when mass production techniques are utilized. In order to overcome the above set forth problems, injection molding techniques are utilized, in the present invention, for the formation of thin walled tubular products. More specifically, handling and formation not only of the resulting tubular products themselves but of the mold parts including mold cavities, core pins, etc. must be dealt with. The primary purpose being to provide a consistent product in terms of structural, dimensional and configurational characteristics. This is especially true when utilizing mass production techniques for medical products wherein safety is frequently a prime concern.

Accordingly, there is a need in the industry for an apparatus and method for producing elongated thin walled tubular products such as, but expressly not limited to, medical catheter type products, preferably but not necessarily using an injection molding technique and an apparatus and method intended specifically for the mass production of a large quantity of such products so as to provide a low cost, safe and reliable thin walled tubular product on which both the industry and the consuming public thereby forming a similar highly undesirable variance in the finished product from its required straight line configuration if such displacement is not corrected or avoided.

The present invention is also directed towards the formation of not only a single product but of a multi-unit production facility wherein the aforementioned elongated tubular products are effectively formed on a continuous basis utilizing what may be referred lo as mass production techniques. Accordingly, in the present invention the injection molding techniques are used in combination with a plurality of mold cavities and an equal number of core pins specifically wherein one core pin is intended and arranged to be utilized with only one of the plurality of mold cavities as set forth in greater detail hereinafter, when the mold pin and mold cavities will be separated and processed separately but concurrently in the treatment and removal of the formed plastic finished product therefrom.

However, in continuously separating and rejoining and aforementioned core pin and mold cavities certain operational characteristics of the subject apparatus and process must be taken into consideration. More specifically, it has been realized that during the injection molding process, certain relatively minimal flow imbalances of characteristics may be associated with the use of a particular mold cavity and core pin combination. This may be due to wear, manufacturing inconsistencies or other reasons which require at least a minimal adjustment of the precise placement of the core pin relative to the mold cavity or interior of the cavity portion generally. Therefore, an important feature of the present invention is the incorporation of an adjustment means. The adjustment means includes a positioning can rely.

SUMMARY OF THE INVENTION

The present invention is directed towards the production of forming thin walled tubular products such as but expressly not limited to medical products including catheters. In the production of such products, great importance is placed on the consistency of the product's dimensional, configurational and of course operational characteristics. Accordingly, in order to overcome problems existing in the prior art with the production of such products, the subject invention includes the utilization of an injection molding technique wherein hot plastic melt is forced, through injection molding into a distributor structure or spider element located at and at least partially defining the entrance to a mold cavity used in the formation of such products. A core pin effectively defining the interior wall surface configuration of the finished product is disposed within the cavity portion of the mold cavity in spaced relation to the interior surface thereof and assumes a straight line configuration along the entire length of the cavity. This is accomplished at least in part by a protruding distal portion of the core pin extending outwardly from the mold cavity. A gripping collet, collet activating means and tensioning means serve to provide axial tension to the core pin. Such tension is maintained until the molding process is completed and the formed tubular product has solidified. It is well known in the molding art that certain forces relating primarily to the force exerted on the core pin during the injection process will tend to displace the core pin from its straight line configuration platform serving to selectively position the mold cavity relative to the core pin or alternately (depending upon the specifical structural embodiment utilized) the combined core pin and mold cavity relative to the injection head serving to channel the hot melt directly into the opening or entrance of the mold cavity about the core pin.

Therefore, an important feature of the present invention is the provision of the adjustment means including a preprogrammable control facility used to control a servomotor mechanism capable of being pre-programmed to "remember" the specific adjusted position coordinates of a given mold cavity and specific core pin combination.

In operation it should be apparent that in a multi-unit production facility, each of a plurality of mold cavities will be associated with specific ones of a plurality of core pins and such mold cavity and core pin combinations will be aligned in the adjusted and preferred position by an adjustment means relative to one another at some time before being clamped into the molding press. Each specific mold cavity and core pin combination will be "recognized" by the adjustment means generally and the control facility thereof in particular. The preprogrammed adjustment positioning of the particular mold cavity and core pin combination will therefore be fed to the servo motor and the molding apparatus, or pertinent portions thereof, will be adjusted in an X-Y plane thereby serving to move the assembly in a plane perpendicular to the longitudinal axis of the mold cavity. This adjusted positioning will in essence be only a minimal distance of travel or displacement and may occur any time prior to injection or introduction of the hot melt into the mold cavity. After injection, the specific mold cavity and core pin combination are removed from the injection mold apparatus and transferred, as a unit, to the next station. The next successive mold cavity and core pin combination will then be fed to the injection ready position and, will be recognized, by the adjustment means generally and the control facility thereof particularly, as a specific mold cavity and core pin combination differing from the others used in the multi-unit production facility. Again, the process will be repeated in that the pre-programmed X-Y co-ordinates of the adjusted positioning of this particular mold cavity and core pin combination will be fed to the servomotors and eventually to the positioning platform which will adjust the appropriate components of the assembly at some time prior to actual clamping of the molding assembly.

Other features of the present invention include the additional manipulation of the mold cavity, core pin and formed plastic part prior to its formation or after injection has taken place. In order to form a relatively large number of such products on a continuous basis it is important to efficiently remove the product from the mold cavity and core pin in which it was formed and perform whatever operational steps on the product found necessary such as trimming, cutting, quality control examination, etc.

Generally, in operation the combined mold cavity, core pin and formed plastic product therebetween will be removed as a unit from the molding press. This combined assembly will then be separated to the extent of removing the combined product and core pin from the cavity. The product and core pin will then be transferred to a first trimming station wherein a conical runner of plastic will be trimmed from the product in automatic fashion and discarded as waste. A core transfer means will remove the combined product and core pin from the trimming site and transfer it to any one of a combination of further processing steps. The still combined product and core pin are then transferred to a product transfer means wherein actual stripping or separation of the product from the core pin is accomplished. The product itself may then be further transferred to a collection facility and prior or subsequent to such transfer, additional trimming or secondary operational procedures may be performed on the product to ready it for packaging.

Another important feature of the present invention is that all of the above transfer means and facilities are driven in a synchronized fashion either through a conventional mechanical linkage, gearing arrangement or other facilities such as a programmable controller which concurrently move the various components including the mold cavity, formed part and core pin first as a united combination; secondly, as a separated mold cavity and combined core pin and product combination; and thirdly, as individual parts including mold cavity separated from the core pin which in turn is separated from the product. The importance of such synchronized movement is the necessity of reuniting a given core pin with the same mold cavity and the placement or positioning of specific core pin and mold cavity combinations in registry with one another and with the aforementioned molding press. This is accomplished to receive the next hot melt injection after the adjustment means accomplishes the aforementioned minimal adjustment of the core pin and mold cavity combination at time prior to the clamping of the molding press. Therefore it should be apparent that regardless of the number of mold cavity and core pin combinations utilized in the subject invention, the reuniting of a given core pin with the same mold cavity will allow the adjustment means to perform the pre-programmed minimal adjusted positioning of this core pin, mold cavity combination at any time prior to clamping of the molding press in order to accommodate or overcome any flow imbalance characteristics and to produce consistent parts. Just as important is the production of a large number of such parts all having a dimensional, structural and configurational consistency even though different mold cavity and core pin combinations are used in their formation.

The invention accordingly comprises the features of construction, combination of elements, and arrangement of parts whiCh will be exemplified in the construction hereinafter set forth, and the scope of the invention will be indicated in the claims.

BRIEF DESCRIPTION OF THE DRAWINGS

For a full understanding of the nature of the present invention, reference should be made to the following detailed description taken in connection with the accompanying drawings in which.

Like reference numerals refer to like parts through out the several views of the drawings.

DETAILED DESCRIPTION OF THE PREFERRED EMBODIMENT

Figures 1, 2:
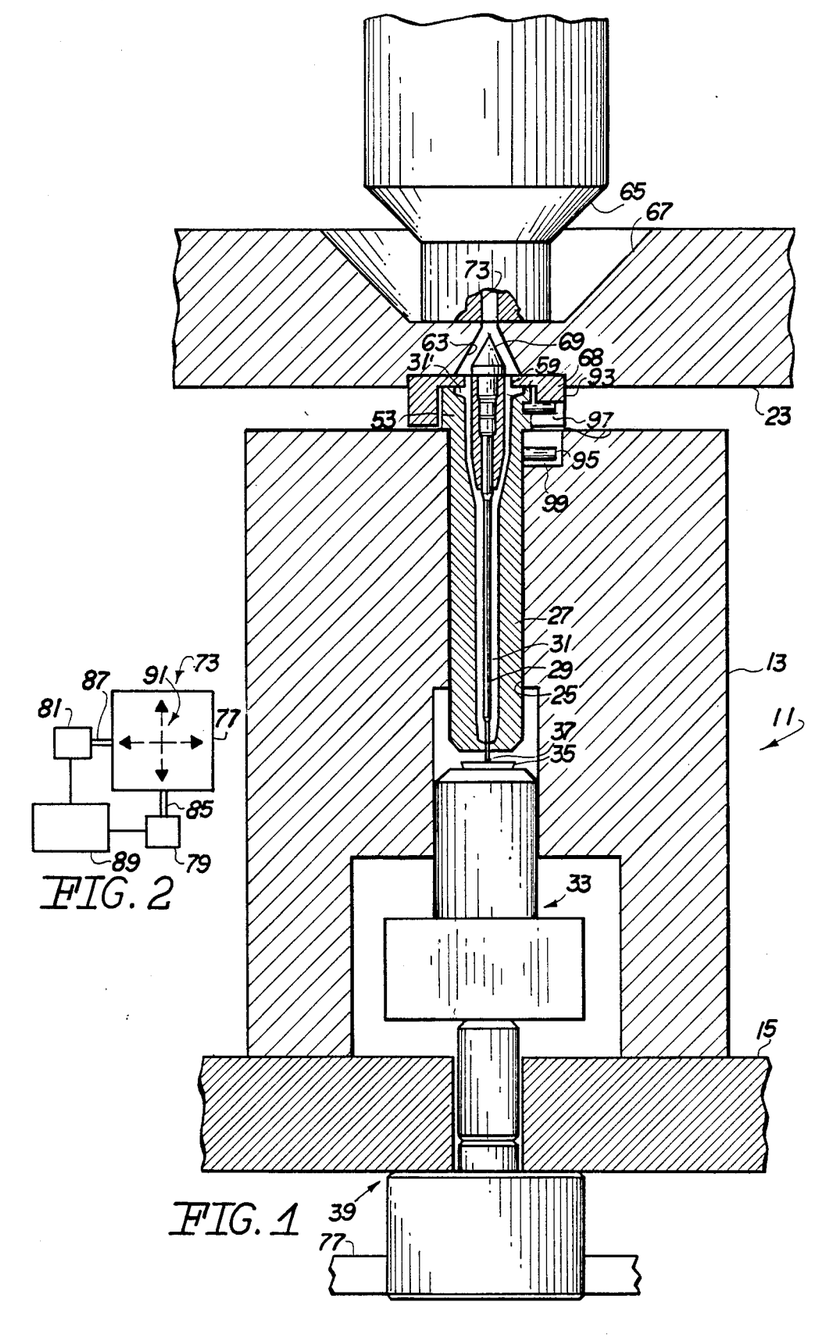
FIG. 1 is a detailed sectional view of a molding assembly of the present invention utilizing a specific combined mold cavity and core pin combination with an injection molding machine and/or press.
FIG. 2 is a schematic representation of the adjustment facility used to adjustably position each of a plurality of mold cavity and core pin combinations prior to camping of the molding press into operative position.

FIG. 1 represents a molding assembly 11 which is intended for use with a commercially available injection molding press such as a 28 ton Arberg or any other like injection molding press facility having applicable performance characteristics. While FIG. 1 relates to an axial in-line injection molding facility wherein the hot melt is directed substantially axially into one open end along the length of the core and in surrounding relation to the core pin, it should be emphasized that the present invention is not limited to an in-line injection molding technique. It is recognized however that under some but not all circumstances, an in-line injection technique is preferred in the formation of the aforementioned type of tubular products. However, while the embodiment of FIG. 1 is shown in combination with the injection molding procedure associated with the formation of a single unit, the present invention is specifically designed for the multi-unit production of such products herein described in a manner which will render each product consistent with the others in terms of dimensional, structural and configurational characteristics. The embodiment of FIG. 1 includes a support member 13 positioned between a lower platen 15 and an upper platen 23. The support member 13 has a central core 25 in which mold cavity 27 is supported and the core pin 29 is maintained under an axially applied tension within the cavity portion 31 of the mold cavity 27. A tensioning means generally indicated as 39 a collet 35 and a collet activating means 33 serve to grip an outwardly protruding distal end portion 37 of the core pin 29 and apply tension thereto. This axial tension is important to the extent of maintaining the core pin 29 in a substantially centered, but not necessarily truly coaxial relation to the cavity 31 of the mold cavity 27. Maintenance of this tension until the formed product has solidified will serve to at least partially overcome the pressure plated on the core pin 29 as the hot plastic melt flows about the core pin 29 in surrounding relation thereto.

The collet actuating means 33 is provided to cause actuation of the tensioning means 39 relative to the collet 35 causing it to close about and fixedly grip the protruding distal end portion 37 of the core pin 29.

In addition to the above, the structure of the present invention provides a spider element or distribution structure 68 is positioned on an upper head portion 53 of the mold cavity 27 and includes a plurality of spaced apart apertures 59 disposed in surrounding relation to a substantially conically shaped deflector pin 69. The spider element 68 including the plurality of apertures 59 serves to channel and direct the inflow of hot melt from the distribution channel 63 formed in platen 23 into the upper entrance of the cavity 27 as at 31' and into surrounding relation to the core pin 29. It should be apparent that the injection nozzle 65 of the injection molding machine is pressed flat against the receiving pocket or channel 67 in the platen 23 and wherein the nozzle aperture 73 is in turn placed in aligned communicating relation with the distribution channel 63 of the platen 23. In the position shown in FIG. 1 the assembly is ready for injection of the hot melt into the cavity 31 through opening 31' of the mold cavity 27 and in surrounding relation to the core pin 29 as the hot melt flows along the length of the core pin 29 and cavity 31. It is again to be emphasized that the injection takes place while the core pin 29 is maintained under constant axial tension due to the gripping of the protruding distal end 37 of the core pin 29 by the collet 35 and subsequent tension applied thereby by tensioning means 39, as set forth above.

An important feature of the present invention is the existence of an adjustment means generally indicated as 73 (schematic representation) and including a positioning platform 77 (see FIG. 1) driven in an X-Y co-ordinates in a plane, considered to be perpendicular, for purposes of reference, to the central axis of the mold cavity 27. Driving of the positioning platform is accomplished by means of two servo motors 79 and 81 and respective associated drive shafts 85 and 87. It is to be emphasized that in the embodiment shown in FIG. 2, the subject adjusting means 73 is represented in schematic form only but importantly it includes a control facility 89. The control facility 89 is preprogrammable and has certain memory characteristics and capabilities as will be explained in greater detail hereinafter. Further with regard to the embodiment of FIG. 1, the positioning platform 77 is associated with the entire mold assembly 11. It is to be emphasized that the placement of the platform 77 is representative only in association with the molding assembly 11 and as shown is positioned so as to drive the entire assembled components including the support member 13, lower platen 15 and tensioning means 39 and collet activating means 33. It is also to be recognized that in actual practical application, the positioning platform 77 of the adjustment means 73 in fact will not be positioned to absorb any significant portion of the force necessarily exerted on the entire assembly 11 when the molding press assumes the operative, clamped position as shown in FIG. 1 prior and during injection of the plastic melt. The actual positioning in FIG. 1 of the positioning platform 77 is provided for purposes of explanation only and is generally considered to be represented in its actual placement relative to the mold assembly 11.

During operation of the subject molding assembly and at any time prior to the clamping of the molding press in the position of FIG. 1, the adjustment means generally indicated as 73 in FIG. 2 will operate to accomplish at least minimal adjustment to balance the flow characteristics of the hot melt along the length of cavity 31. More specifically, control facilities 89 is capable of being preprogrammed and will activate servo motors 79 and 81 serving to drive the positioning platform 77 in either or both on X and Y direction as generally represented by X-Y coordinates 91. Therefore, any specific "flow imbalance characteristics" of a particular mold cavity 27 and core pin 29 combination, with which it is always used, will be previously determined and stored into a memory facility associated with the control assembly 89. The recognition by the control facility 89 of the automatic adjusting means 73 of a particular mold cavity 27 and core pin 29 combination to be injected, will serve to control the specific minor positioning adjustments, along an X-Y axis by "remembering" the preprogrammed X-Y coordinates for that particular Core pin, mold cavity combination at some time prior to assuming the clamped and injection ready position as shown in FIG. 1. The referred to X-Y positioning or X-Y axis is to be considered specific distances or amounts of displacements in the respective X-Y axis of a perpendicular plane to the axis of the injection nozzle 65 to accommodate and overcome any of the aforementioned flow imbalance Characteristics which may be associated with a particular mold cavity, core pin combination. Such inconsistencies or flow imbalance characteristics may be due to manufacturing inconsistencies, surface characteristics, wear, or any other factor which must be overcome in order to insure that a particular mold cavity, core pin combination will produce on a continuous basis, an elongated plastic thin walled tubular product having a straight line configuration.

Other structural features associated with the specific embodiment of FIG. 1 include the provision of stabilizing pins 93 and 95 which pass into open ended slots 97 and 99 respectively so as to further stabilize the mold cavity 27 relative to the spider element 47 (by pin 93 and slot 97) and the mold cavity 27 with regard to the support member 13 (by pin 95 being placed in slot 99). The plaCement of a stabilizing pins 93 and 95 in the aforementioned position serve to prevent relative rotational movement and therefore general stabilization.

With reference to FIGS. 3 through 13, an important feature of the present invention is the multi-unit production facility generally indicated as 10 and including a support base or platform 12 positioned in direct communication and cooperation with an injection site generally indicated as 14. In terms of an injection site 14, the molding assembly 11 (see FIG. 1) and associated adjustment means (see FIG. 2) are located at the site and are appropriately positioned relative to the plurality of transfer means 16, 18 and 20 to be described in greater detail hereinafter. For purposes of clarity, the site of the molding assembly 11 is only generally represented as 14 and the actual components used are disclosed in detail in FIGS. 1 and 2 and ar not provided in the representation of FIG. 3.

Figure 3:
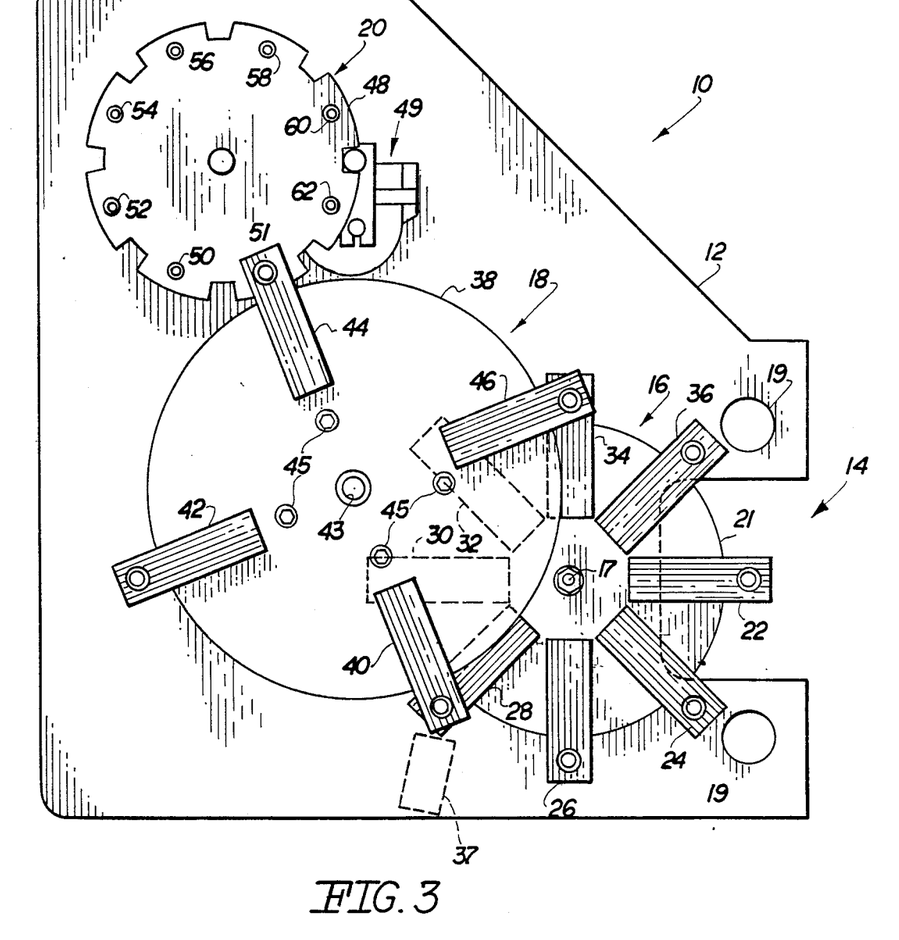
FIG. 3 is a top elevational view of a multi-unit production facility and a plurality of transfer facilities associated therewith.

As shown in FIG. 3, the support base or table 12 properly positions a plurality, preferably at least 3 transfer stations including cavity transfer means 16, core transfer means 18 and product transfer means 20 all in operative relation to one another so that the individual components including the mold cavity 27, finished part 114 and core pin 29 transferred from the injection site 14 as a combined unit, can be respectively separated and independently carried, manipulated and processed, all in synchronization. Further, the mold cavity 27 and core pin 29, after separation from the finished product, are then reunited to be combined at the injection site 14 with one another and the molding assembly 11 (see FIG. 1) to be reinjected and to continuously and repeatedly form a plurality of the plastic parts 114.

Figure 4:
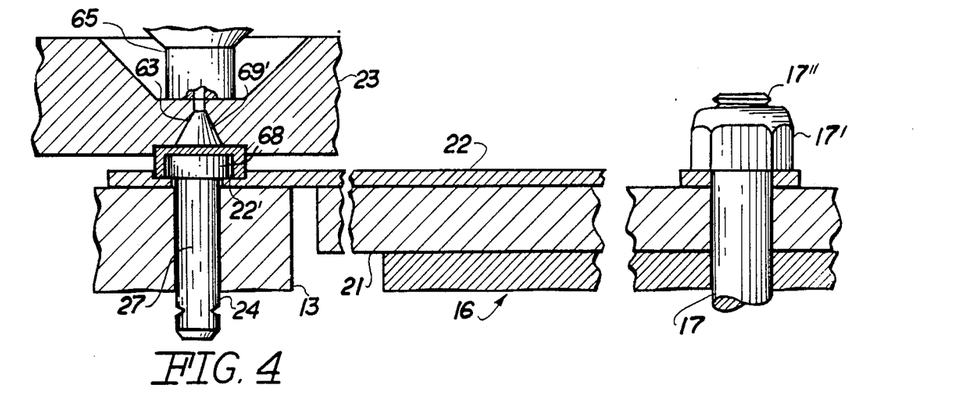
FIG. 4 is a sectional view in partial cross-section of a first transfer station and a mold cavity and core pin combination prior to removal from the injection molding press.
Figure 5:
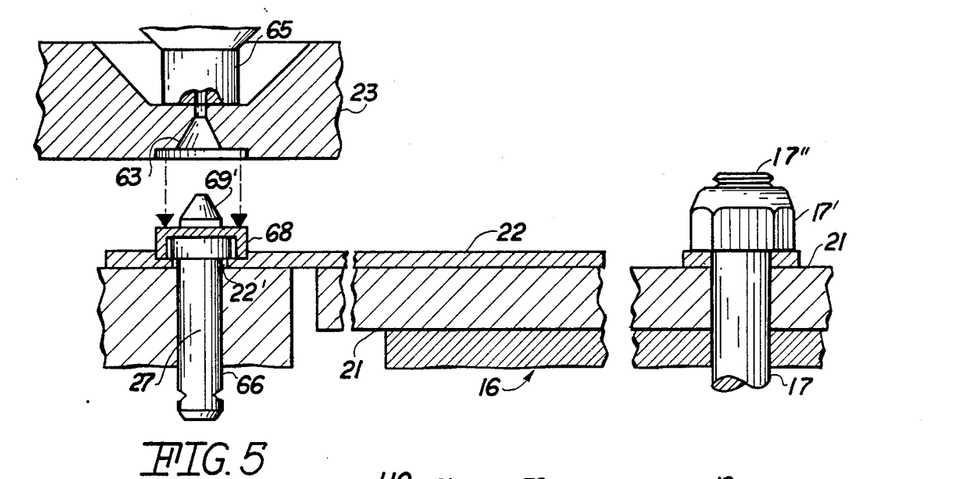
FIG. 5 is a detailed cross-sectional view in partial cutaway of the aforementioned combination being removed from the molding press.
Figure 6:
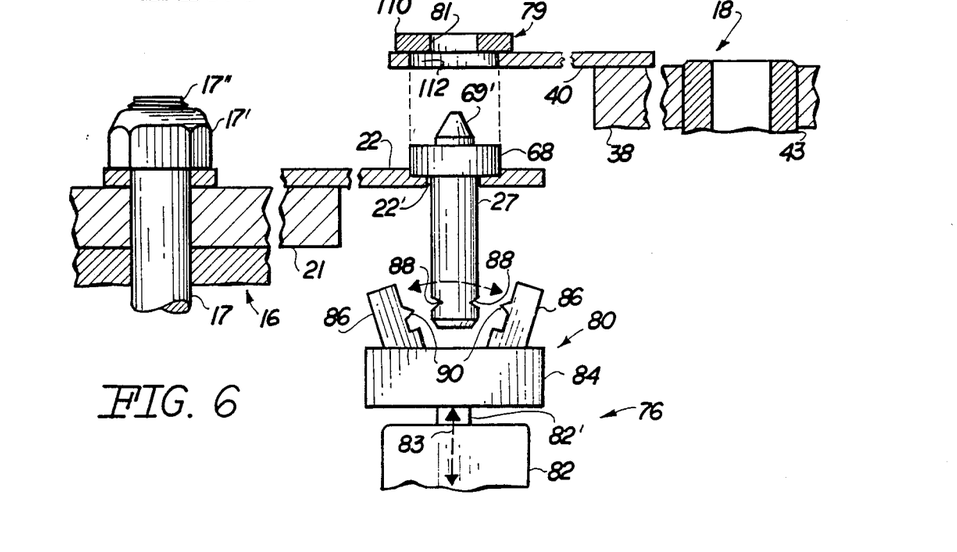
FIG. 6 is a view in partial section and cutaway of the transfer station associated with FIGS. 3 and 4 and a second transfer station associated therewith.

With regard to FIGS. 3 through 6, the cavity transfer means 16, in the embodiment shown, includes a rotationally mounted core transfer plate 21 having a plurality of carrying arms 22, 24, 26, 28, 30, 32, 34 and 36 all disposed in spaced apart relation to one another and all having an end configuration (see FIGS. 4–6) being apertured and/or otherwise structured as at 22' to removably support one mold cavity 27 and associated finished part 114 and core pin 29 inside the cavity 31, wherein only the spider element 68 is shown in FIGS. 4–6 for purposes of clarity. It is again emphasized that each of the arms 22–36 will be carrying a separate combined mold cavity, core pin and formed product combination which will be repeatedly removed from and positioned at the injection site for successive formation of a new product.

As the cavity transfer plate 21 rotates, the particular arm 22 described herein, will be advanced, on a step-by-step basis, until a point where it reaches the second transfer means or core transfer means 18 is defined by core transfer plate 38 also rotatably mounted by a shaft mechanism 43 to the support base or platform 12 (see FIG. 3).

Further with regard to FIGS. 4–6, a rotating support shaft 17 secures the mold transfer means 16 to the support platform 12 as shown in FIG. 3 and serves to provide a component of the synchronized drive to be explained in greater detail hereinafter. FIG. 6 represents the position of the arm 22 and associated mold cavity 27, combined spider element 68 and a plastic runner cap 69' which is a waste part formed over distribution tip 69 secured to the product (not shown) which is on the interior of mold cavity 27. The runner 69' is to be removed and discarded and is formed by the hardening of the plastic melt over the distribution tip 69 as shown in FIG. 1.

Further with regard to FIG. 6, the second core transfer means 18 is in aligned registry with the cavity transfer means 16. More specifically, receiving or carrying arm 40 (also see FIG. 3) of the core transfer means 18 is disposed in aligned registry with the first carrying arm 22 of the cavity transfer means 16. The arm 40 as well as each of the arms 42, 44 and 46 of the core transfer means 18 are mounted to rotate with the core transfer plate 38. Each arm, including arm 40, has an outwardly extending carrier fixture 79 and an aperture 112 formed in the arm 40. The carrying fixture 79 is preferably magnetic, and which includes a central aperture 81 for the receipt of the distribution cone 69. In this position the waste plastic runner element 69' is still contained thereon. It should be apparent from an understanding of FIGS. 6, 7, 8, 8A and 9 that the carrier fixture 79 comprises a magnetic element 110 formed from magnetic material and disposed to include the aforementioned central aperture 81 for passage therethrough of the conical runner 69'. The magnetic material element 110 accordingly serves to magnetically attract and thereby support the spider element 68 but is of such strength to allow displacement and removal of the spider element 68 and mold cavity 27 in a manner to be described in greater detail hereinafter.

Further with regard to FIG. 6, a first positioning means 76 includes an air cylinder or like drive motor 82 having capabilities of raising and lowering the shaft 82' in a vertical direction in accordance with the directional arrow 83. In addition, clamping jaws 86 are disposed into communicating engagement with what may be considered a lower portion of the mold cavity 27 and more specifically notches 88 or other indentations formed on mold cavity 27, which may be gripped by teeth 90 secured to the respective jaws 86. The jaw operating mechanism 84 may be considered a part of positioning means 76. The jaws 86 may be selectively positioned into and out of clamping engagement with the mold cavity 27 (see FIGS. 6, 7, 8 and 8A) for purposes of gripping the exterior indentations 90 on the mold cavity 27. Once gripped, the mold cavity 27 may be dislodged from its supported position on the arm 22 and within the aperture 22' thereof by raising the shaft 82'.

Accordingly, the purpose of the positioning means 76 is to effectively lift the combined mold cavity 27, spider element 56 and enclosed finished product (not shown) out of the carrying arm 22 of the mold transfer means 16. The distance the mold cavity and spider element is raised allow access therebeneath of a second lifting assembly generally indicated as 100 in FIGS. 7 and 8.

Figures 7, 8, 8A, 9:
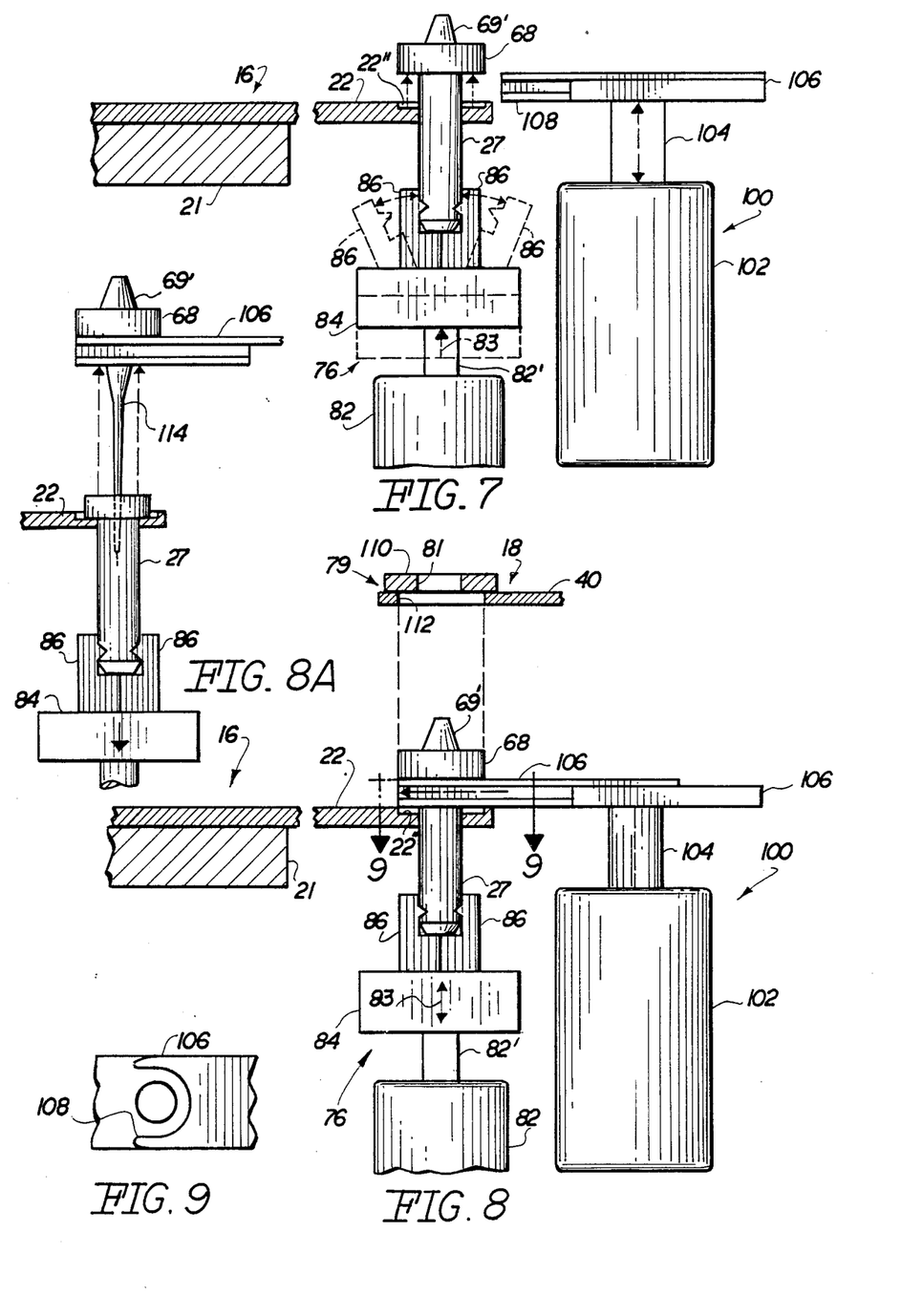
FIG. 7 is a sectional view in partial cutaway of the first transfer station and a positioning and removal facility associated therewith.
FIG. 8 is a sectional view in partial cutaway of the first and second transfer station disposed relative to accomplish transfer of the core pin and combined product immediately prior to separation from the mold cavity.
FIG. 8A is a sectional view in partial cutaway of the next step in removing the mold cavity from the formed product and core pin.
FIG. 9 is a detailed top plan view in partial cutaway of the lifting o transfer facility associated with the embodiment of FIG. 7.

With regard to FIGS. 7 and 8, and in operation, the air cylinder 82 of the first lift mechanism 76 is activated causing an upward stroke as indicated by directional arrow 83. Concurrently or previously thereto the jaw activating mechanism 84 serves to close the jaws from their open position (see phantom lines in FIG. 7) to their closed clamping position relative to the mold cavity 27 or more particularly the exterior portion thereof. As further shown the mold cavity 27 therefore extends outwardly from and through the aperture 22' in the carrying arm 22 a sufficient distance for supporting and carrying engagement with the carrying arm 106 (see details FIG. 9) which has an open carrying end as at 108. Once the mold cavity 27 assumes the position as shown in FIG. 7, the arm 106 is rotated or otherwise positioned in an underlying and supporting position relative to the spider element 68. Due to the gripping action still being applied to the lower portion 66 of mold cavity 27 by jaws 86, a downward stroke is exerted on the shaft 82' by the air cylinder 82 causing at least a partial dislodgement and separation of the mold cavity from the product, core pin and spider element 68 (see FIG. 8A). The spider 68 carrying the finished produCt (not shown) will be maintained in supported engagement with the positioning arm 106. The existence of the countersunk recess 22" will serve to support the head portion 53 (see FIG. 1) of the mold cavity 27 as it is completely separated and removed from the finished product and core pin now being carried by the transfer arm 106 of the second positioning means 100. As further shown in FIG. 8, the transfer mechanism 100 continues to travel upwardly until the spider element 68, formed of metallic material, engages the magnetic holder 110 being part of the arm 40 which in turn is secured to and rotates with the core transfer plate 38 of the Core transfer means 18. Concurrent to this, the first positioning means 76 releases the mold cavity 27 for continuous step-by-step advancement and travel with the mold transfer means 16 in the arm 22 (FIG. 3).

Figures 10, 11, 12:
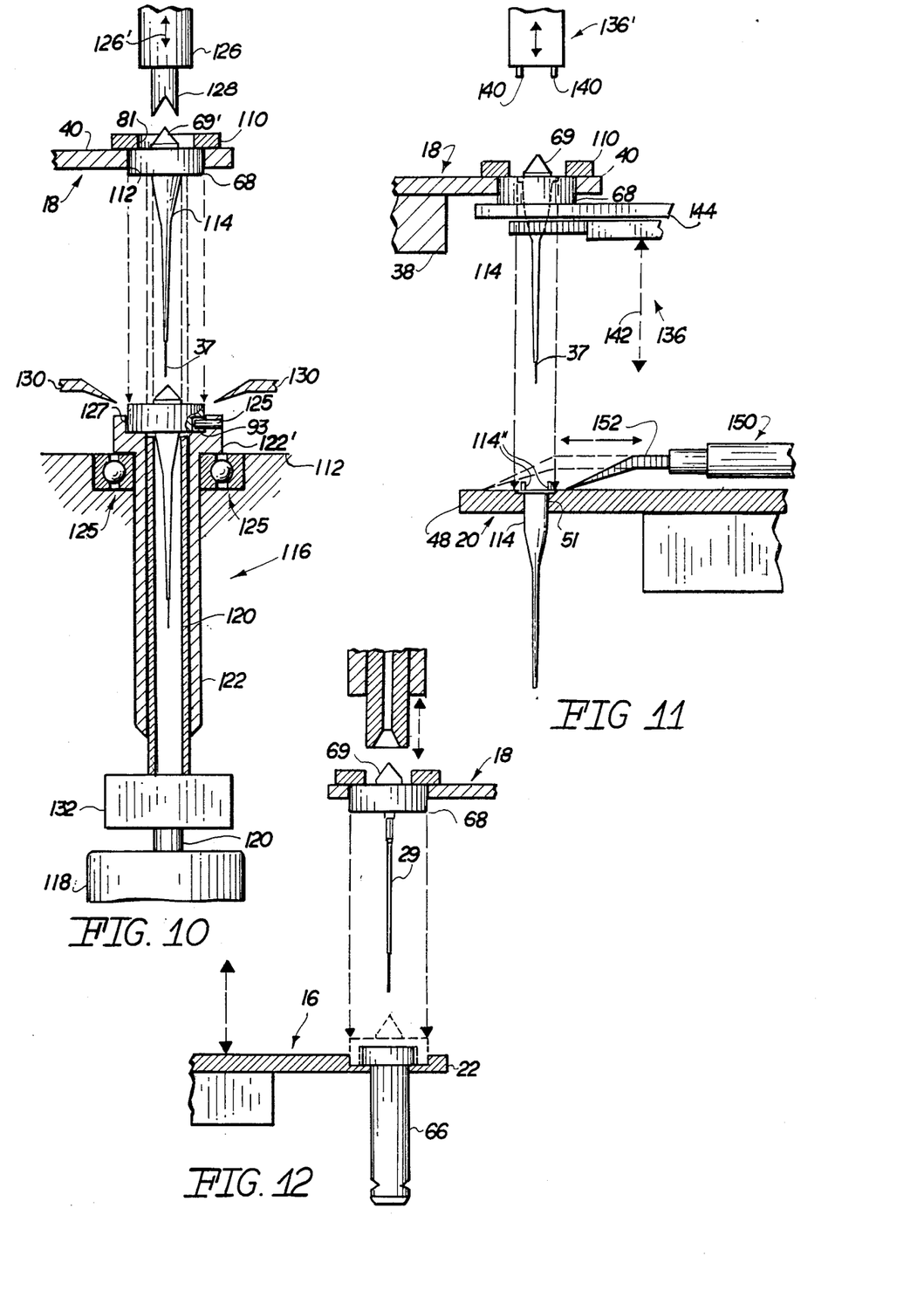
FIG. 10 is a sectional view in partial cutaway of the second transfer station associated with a trimming device and a placement facility for properly positioning the combined product and core pin relative thereto.
FIG. 11 is a sectional view in partial cross-section of the second and a third transfer station and facilities provided for separation of the product from the core pin and the performance of a trimming operation on the product.
FIG. 12 is a sectional view in partial cutaway of the second and first transfer station and an associated placement or positioning facility associated therewith to accomplish the reuniting of a specific core pin with a specific mold cavity to form one of a plurality of core pin, mold cavity combinations.

With reference to FIG. 10, the core transfer means 18 continues to advance in a circular fashion passing through the stations indicated in FIG. 3 by arms 42 and 44 of the core transfer means 18. As set forth above, other procedural steps in terms of quality control examination or other manipulative steps may be done to the now exposed product 114 (FIG. 10) or the other portions of the combined core pin (distal end 37) or still existing and present cone runner 69'.

FIG. 10 further shows a cutting or trimming station generally indicated as 116 which is specifically provided for the removal of the cone runner 69'. The trimming station 116 includes an air cylinder or like lifting member 118 serving to drive in a vertically upward or downward stroke shaft 120 located within a surrounding centrally disposed sleeve 122 and movable along its axis relative thereto. Bearing members are provided and generally indicated as 125 and allow relative rotation of the external sleeve 122 to the support member 112 and the central shaft 120. A stabilization member 126 having an engaging finger 128 is also provided at this locale and is capable of moving axially in accordance with the directional arrow 126' as shown. In operation, the central shaft 120 raises up through the support plate 112 into engagement with the lower portion of the spider 68 and/or product 114. This occurs concurrently to the downward positioning of the stabilization member 126 and finger 128, the latter being shaped to engage the runner 69'. Once so positioned, the entire product 114, spider element 68 and runner 69' move downwardly through the central aperture 112 and 81 of the holder and arm 110 and 40, respectively, so that the spider 68 is placed in a fixed position within the recess 127 on the enlarged head 122' of the rotatable outer sleeve 122 ready for access to the blades 130. The spider 6B and finished part 114 are then rotated by a rotating actuation device 132 causing relative rotation of the combined runner 69', spider 68 and product 114 due to its engagement with the rotatable sleeve 122 and the bearings 125. In this position and during rotation, the shaft 120 will be spaced out of engagement with the under portion of spider 68. During the rotation, the blades 130 are moved inwardly in accordance with the directional arrows as shown in FIG. 10 thereby completely severing the cone runner 69' and exposing the distribution cone 69 as originally shown in FIG. 1. The runner 69' is discarded in any convenient manner and the shaft 120 is again extended upwardly to reestablish magnetic contact and support of the still combined product 114 and spider 68.

With regard to FIG. 11, a gripper and separator mechanism generally indicated as 136 and 136' are used in cooperation with the continued transfer and support of the core pin 29, spider 68 and exposed distribution cone 69. As shown in phantom lines in the upper portion of FIG. 11, the finished product 114 is considered to be still in place in combination and about the core pin 29. Removal therefrom occurs by a downward travel of a removal arm 136' having a plurality of teeth 140 designed to fit within the apertures 59 of the spider element 68 (see FIG. 1) and literally push the finished product, now solidified, from its tight engagement with the spider element 68 (FIG. 11). Such occurs simultaneously to a downward travel of the gripper element 136 through any adaptable facility as indicated by directional arrow 142. A support plate 144 serves to maintain the spider element 68 in its fixed position relative to support and transfer by the arm 40 and workholder 110.

The finished product 114 is then brought down to its supported position in the third product transfer means more specifically comprising the product transfer plate 48 within an appropriately configured and dimensioned bore 51. It should be further noted in FIG. 11 that outwardly projecting fingers 114' still attached to the finished part 114 project outwardly or above the surface of the product transfer plate 48 but are removed from part 114 through a reciprocal cutter facility generally indicated as 150 including blade 152. Since the fingers 114' are the only projections from the flush engagement of the upper portion of the product 114 relative to the product carrier plate 48, a single stroke can sufficiently remove all the projecting fingers 114' therefrom as should be readily apparent. Accordingly, it should now be apparent that the product 114 is effectively finished, trimmed, treated, etc. and is being carried solely by the third product transfer means 20 including the transfer plate 48 into a plurality of various positions indicated by the receiving apertures 50–62 as shown in FIG. 3. Table interlock 49 (see FIG. 3) indicates an interlocking mechanism clearly associated with the plate or table 48 but in fact being representative of any number of interlocking devices serving to correspond the rotational movements of the rotational tables or plates as dicussed above. Other steps that may be taken relative to the finished product 114 is the removal therefrom to a collection facility or for other auxiliary or supplementary processing thereof. It should further be noted that the product in fact can be removed from any of the tables after only completing a portion of the processing step associated therewith.

Figure 13:
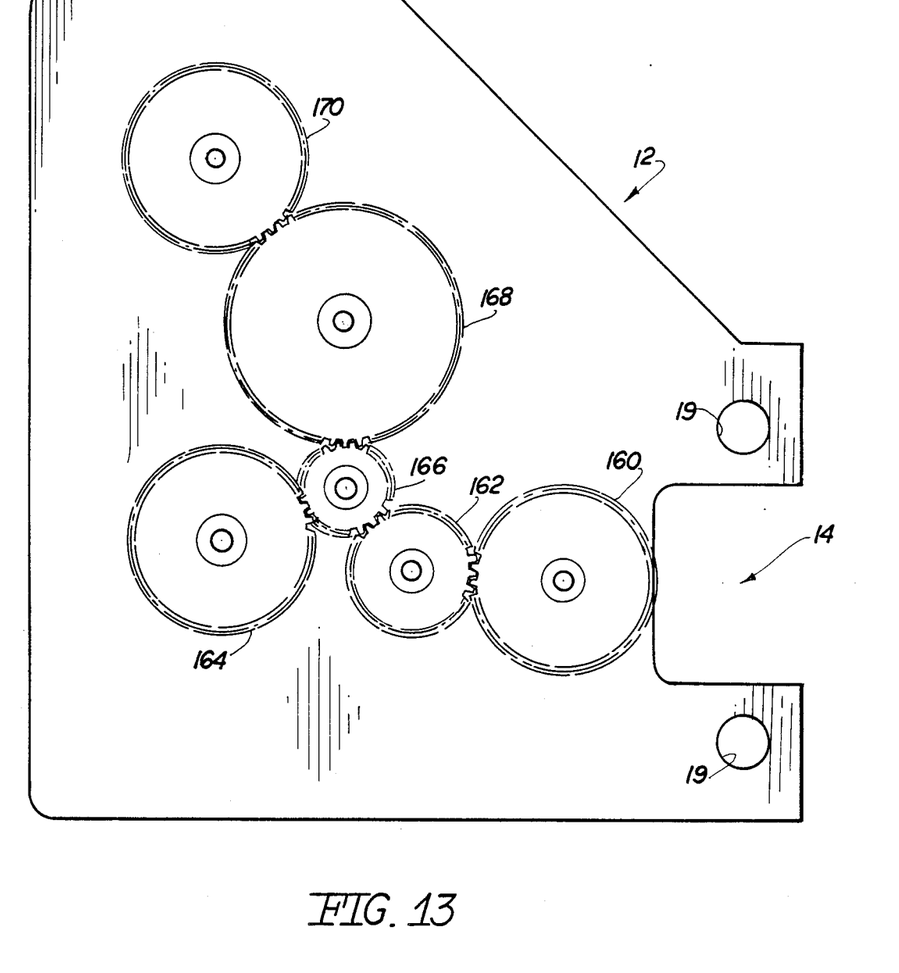
FIG. 13 is a top elevational view in partial section and schematic form showing a drive mechanism for the plurality of aforementioned transfer stations.

In addition to the various processing steps as described above, it is important to note with regard to FIG. 13 that a plurality of driving and idler gears 160, 162, 164, 166, 168 and 170 all may be interconnected to one another so as to be interconnected to and effectively cause synchronized driving or movement of the various individual mold cavity, core pin and product component not only during their individual manipulative steps but in a manner which will serve to specifically reunite the same mold cavity with the same core pin after the mold cavity is separated from the core pin and product combination and subsequently after the core pin is separated from the product. It should further be noted that while in FIG. 1 eight arms are shown, each intended to carry a different mold cavity and core pin combination and subsequently four arms were shown each intended to carry a different product and core pin combination, any number of combined arms may be utilized. The invention is not limited merely to eight initial carrier arms on the cavity transfer plate 21.

It should also further be pointed out that the mechanical linkage or gearing facility serving as a drive mechanism is provided by way of one method of accomplishing the required synchronized movement of the mold transfer means 16, core transfer means 18 and product transfer means 20 so as to reunite and mate the same mold cavity 27 with the same core pin 29 prior to repositioning at the injection site 14 and the clamping of the molding press for the formation of another product. Other individual drive mechanisms could be used and the required synchronization could occur by regulating a plurality of independent drive motors for example.

It is therefore to be understood that the following claims are intended to cove all of the generic and specific features of the invention herein described, and all statements of the scope of the invention which as a matter of language, might be said to fall therebetween.

Now that the invention has been described,
What is claimed is:

1. A method of transferring and processing a plurality of continuously produced molded tubular products formed by a mold cavity and a core pin combined in a specific cavity and core pin pair comprising the steps of:
   (a) transferring the combined formed product and cavity and core pin pair as a unit away from a molding site,
   (b) separating the mold cavity from the product and still combined core pin,
   (c) transferring the combined product and core pin from the locale of separation of the mold cavity therefrom to a local for separation of the product and core pin,
   (d) separating the product from the core pin and subsequently transferring the product separated from the core pin and independently therefrom to a collection facility,
   (e) concurrently to independently transferring the product, independently transferring the mold cavity and the core pin in segregated relation to one another into a reunited cavity and core pin pair at least at the molding site,
   (f) adjusting each reunited cavity and core pin pair immediately prior to receipt of a hot plastic melt therein in accordance with preselected X-Y coordinates relative to the point of introduction of the hot melt into the cavity and core pin pair, and
   (g) preselecting a plurality of X-Y coordinates, each in association with individual ones of a plurality of cavity and core pin pairs and thereby regulating inflow and balance characteristics of the hot plastic melt to be injected into each of the plurality of cavities and core pin pairs.

2. A molding and transfer assembly for the successive injection molding, transfer and processing of a plurality of elongated thin walled tubular products, said assembly comprising:
   (a) a plurality of cavity and core pin pairs each of which include;
      (1) a mold cavity having an open end and including an interior having a surface configured to define the exterior surface of one tubular product and positioned to receive a flow of melt into said mold cavity; and
      (2) a core pin disposed on said interior of said mold cavity and having an elongated, straight line configuration and being spaced from said interior surface of said mold cavity along a major portion of its length;
   (b) a tensioning means mounted exteriorly of said mold cavity adjacent an end thereof opposite to said open end and attachable to an exterior portion of said core pin for placing axially applied tension thereon,
   (c) distribution means disposed to receive an inflow of injected melt and further disposed in communication with said interior of said mold cavity and structured for distributing the melt in surrounding relation to the core pin,
   (d) an adjusting means connected to said mold cavity for regulating flow and balance characteristics of the melt to be injected relative to each of said plurality of cavity and core pin pairs,
   (e) a plurality of transfer stations collectively structure for successive separation of said mold cavity, each structurally adapt to successively separate said mold cavities, core pins, and products from one another, and
   (f) said plurality of transfer stations structurally adapted for the successive and continued realignment of specific individual ones of mold cavities with specific individual ones of core pins to successively reunite and position each of said plurality of cavity and core pin pairs at an injection site.

3. An assembly as in claim 2 wherein said plurality of transfer stations include at least a first transfer means and a second transfer means structured and disposed in mutually synchronized operation relative to one another for the successive reuniting of specific mold cavity with specific core pin to form specific ones of said plurality of cavity and core pin pairs.

4. An assembly as in claim 3 wherein said plurality of transfer stations further comprise at least a third transfer means disposed in communicating relation with at least one other of said first and second transfer means for the transfer of the product independently of said mold cavity and said core pin of each of said cavity and core pin pairs, to a collection facility.

5. An assembly as in claim 2 wherein said adjusting means comprises a control means including a memory capability for recognizing and determining each of a plurality of X-Y coordinates associated with individual ones of said plurality of cavity and core pin pairs.

6. An assembly as in claim 5 wherein said control means is structured to be preprogrammed for the storage of said plurality of X-Y coordinates, each of said plurality of X-Y coordinates being assigned to an individual one of said plurality of cavity and core pin pairs.

7. An assembly as in claim 6 wherein said adjusting means further comprises a positioning assembly interconnected in driving relation to successive ones of said cavity and core pin pairs at a molding site and further connected to said control means for activation thereof by said control means.

8. An assembly as in claim 7 wherein said positioning assembly comprises a positioning platform interconnected successively to each of said cavity and core pin pairs, positioned driving means operatively connected to said control means and interconnected between said control means and said positioning platform for selective positioning of said platform, said positioning platform and associated cavity and core pin pairs selectively positionable relative to an inflow of plastic melt at a designated, preprogrammed X-Y coordinate upon activation of said control means.

9. A transfer assembly designed for use in the continuous production and processing of a plurality of molded tubular products formed by a molded cavity and a core pin positioned on an interior of the mold cavity, said assembly comprising:

(a) a plurality of transfer stations structurally adapted to successively separate said mold cavities, core pins and product from one another, (b) said plurality of transfer stations including at least a first transfer means disposed and structured to support and transfer the plurality of products and combined cavity and core pin pairs thereof from a molding site, (c) said plurality of transfer stations including at least a second transfer means disposed and structured for transfer of each of the plurality of products and associated individual core pins associated therewith from said first transfer means in segregated relation to individual ones of the mold cavities, (d) said plurality of transfer stations including at least a third transfer means disposed and structured for transfer of each of the plurality of products from said second transfer means in segregated relation to individual ones of the core pin, (e) drive means interconnected to said plurality of transfer stations and structured for selective synchronized positioning of at least some of said plurality of transfer stations relation to one another, (f) said first and said second transfer means each connected to said drive means and driven in synchronized relation to one another and structured for continuous and successive reuniting of specific mold cavity with specific core pins to define specific cavity and core pin pairs at least at said molding site, (g) an adjustment means connected to said cavity and core pin pairs for regulating inflow and balance characteristics of the melt introduced thereto relation to each of the plurality of cavity and core pin pairs, and (h) said adjusting means comprising a control means including a memory capability for recognizing and determining each of a plurality of X-Y coordinates associated with individual ones of said plurality of cavity and core pin pairs.

10. An assembly as in claim 9 wherein said control means is structured to be preprogrammed for the storage of said plurality of X-Y coordinates, each of said plurality of X-Y coordinates being assigned to an individual one of said cavity and core pin pairs.

11. An assembly as in claim 10 wherein said adjusting means further comprises a positioning assembly interconnected in driving relation to said cavity and core pin pairs at said molding site and further connected to said control means for activation of said positioning assembly by said control means.

12. An assembly as in claim 11 wherein said positioning assembly comprises a positioning platform interconnected successively to each of said cavity and core pin pairs, position driving means operatively connected to said control means and interconnected between said control means and said positioning platform, said positioning platform and associated cavity and core pin pairs selectively positionable relative to an inflow of plastic melt at a designated preprogrammed X-Y coordinate upon activation of said control means.

* * * * *